US010883995B2

(12) United States Patent
Ahmed

(10) Patent No.: US 10,883,995 B2
(45) Date of Patent: Jan. 5, 2021

(54) METHODS AND SYSTEMS FOR MANAGING THE TEMPERATURE OF MEDICINES

(71) Applicant: Faizan Ahmed, San Jose, CA (US)

(72) Inventor: Faizan Ahmed, San Jose, CA (US)

( * ) Notice: Subject to any disclaimer, the term of this patent is extended or adjusted under 35 U.S.C. 154(b) by 262 days.

(21) Appl. No.: 16/134,192

(22) Filed: Sep. 18, 2018

(65) Prior Publication Data
US 2019/0137506 A1    May 9, 2019

Related U.S. Application Data

(63) Continuation-in-part of application No. 15/939,267, filed on Mar. 28, 2018, now abandoned.

(60) Provisional application No. 62/477,598, filed on Mar. 28, 2017.

(51) Int. Cl.
| | |
|---|---|
| *G01K 1/00* | (2006.01) |
| *G01K 13/00* | (2006.01) |
| *G01K 7/00* | (2006.01) |
| *G01N 33/66* | (2006.01) |
| *G01K 1/02* | (2006.01) |
| *A61J 1/00* | (2006.01) |

(52) U.S. Cl.
CPC ............... *G01N 33/66* (2013.01); *A61J 1/00* (2013.01); *G01K 1/02* (2013.01); *G01K 1/024* (2013.01); *A61J 2200/72* (2013.01)

(58) Field of Classification Search
USPC .................................. 374/142, 141, 208, 163
See application file for complete search history.

(56) References Cited

U.S. PATENT DOCUMENTS

| | | | | |
|---|---|---|---|---|
| 2004/0247016 | A1* | 12/2004 | Faries, Jr. ............. | A61B 50/13 374/162 |
| 2008/0052044 | A1* | 2/2008 | Shoenfeld .......... | G07C 9/00896 702/188 |
| 2010/0305421 | A1* | 12/2010 | Ow-Wing ............... | H04W 4/80 600/365 |
| 2015/0253205 | A1* | 9/2015 | Hauser ..................... | G01K 1/20 374/170 |
| 2016/0058661 | A1* | 3/2016 | Pether ................... | A61J 7/0454 455/557 |
| 2016/0071015 | A1* | 3/2016 | Tateno ................... | G06N 20/00 706/11 |

* cited by examiner

*Primary Examiner* — Mirellys Jagan

(57) ABSTRACT

A computer-implemented process useful for implementing a medometer management application including the step of, with a temperature sensor operative in the medometer, obtaining a temperature value of a medicine, a test strip and a medical device. With the medometer, the process includes the step of formatting the temperature value of the medicine for communication via a wireless network and communicate the formatted temperature value to a mobile device via a wireless network. With a medometer management application operative in the mobile device, the process includes the step of displaying the temperature value to a user.

15 Claims, 19 Drawing Sheets

500

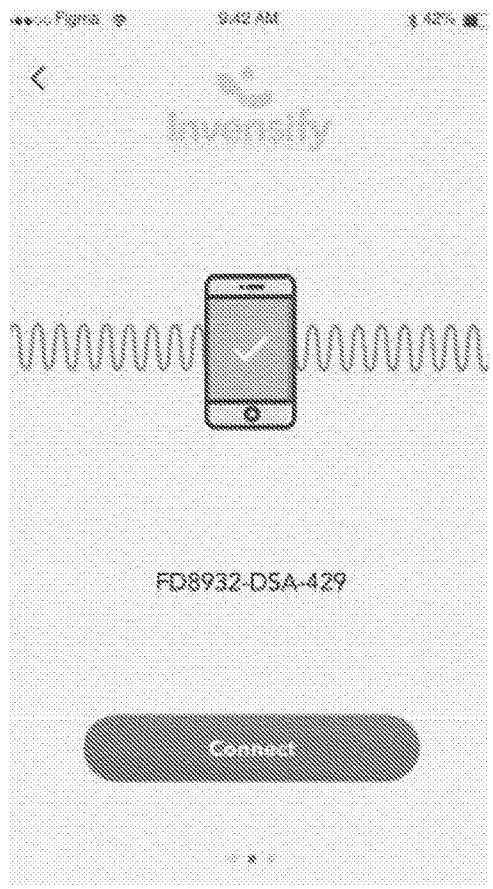
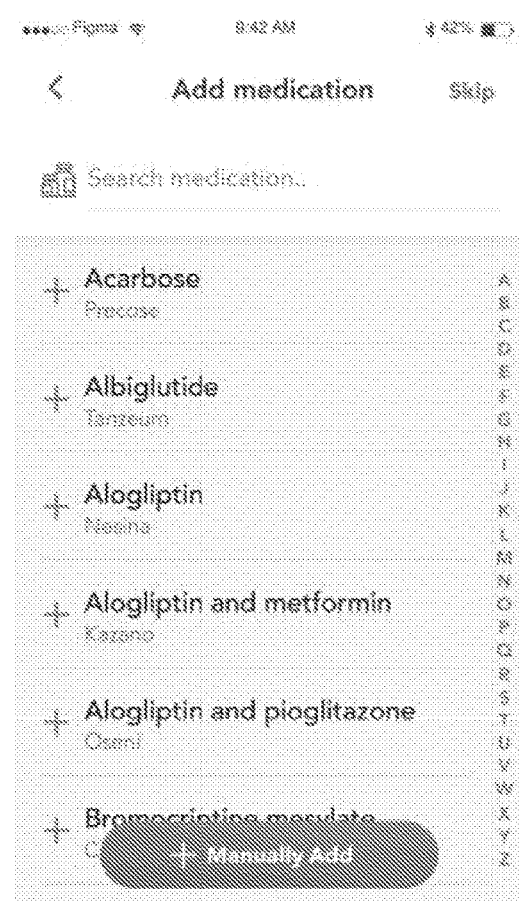
FIGURE 5C
FIGURE 5D
500

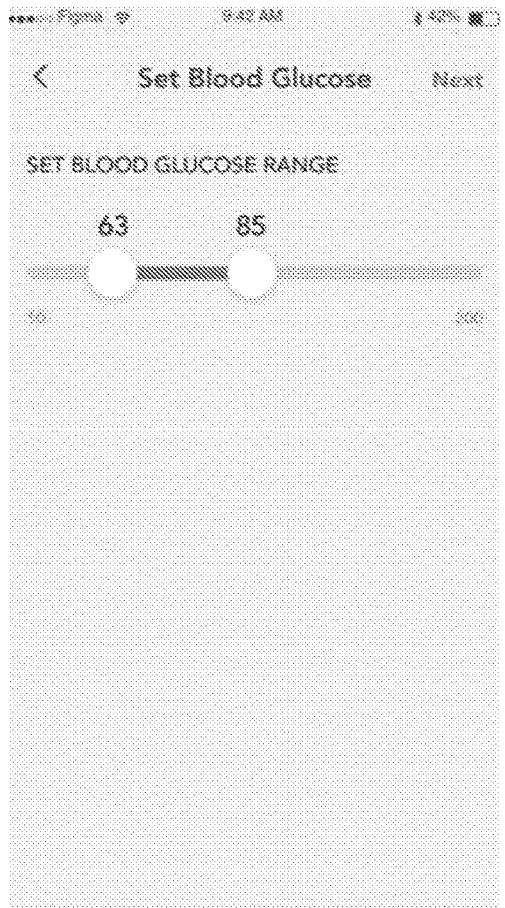
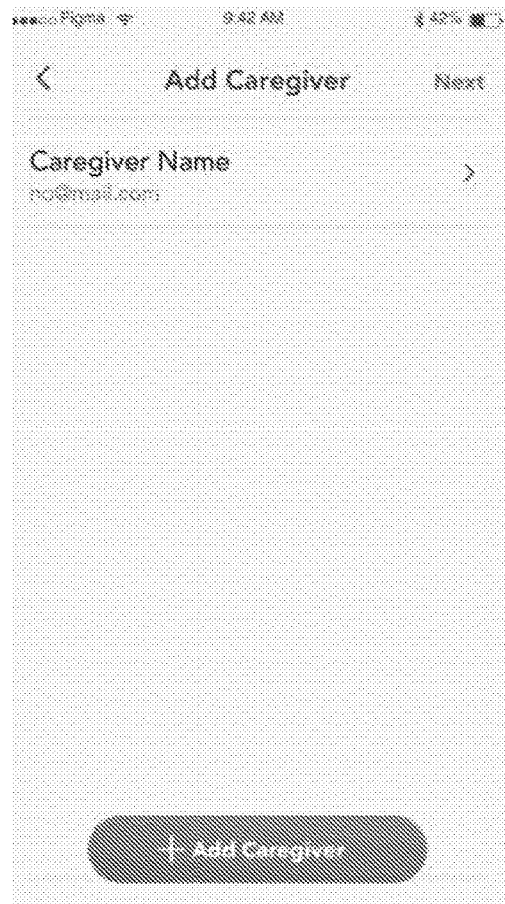
FIGURE 5I
FIGURE 5J
500

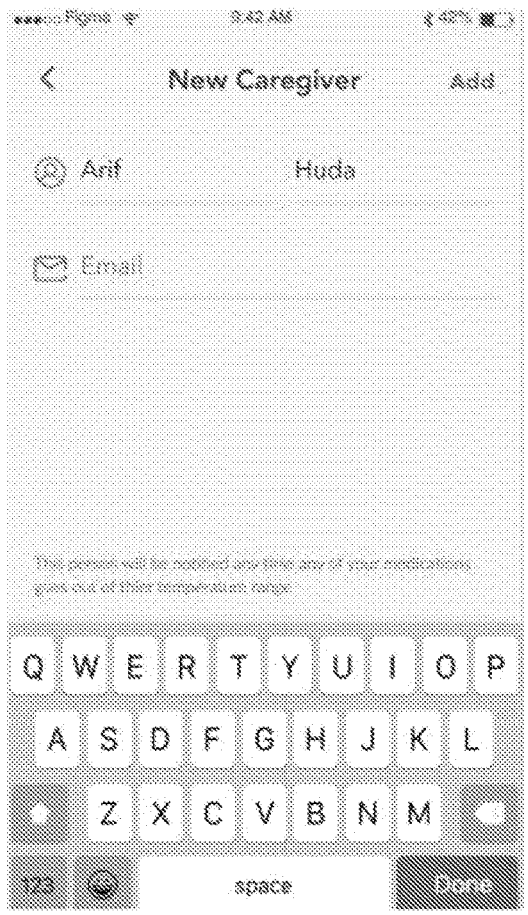
FIGURE 5K
FIGURE 5L
500

500

500

500

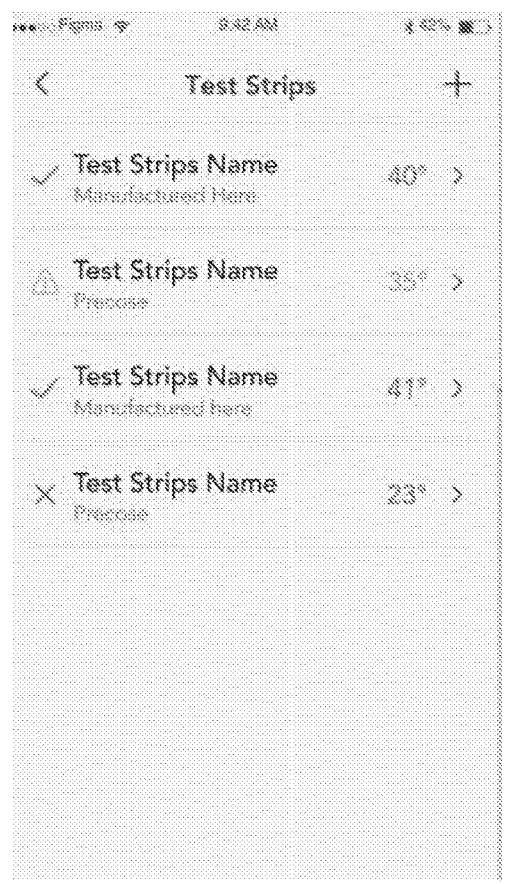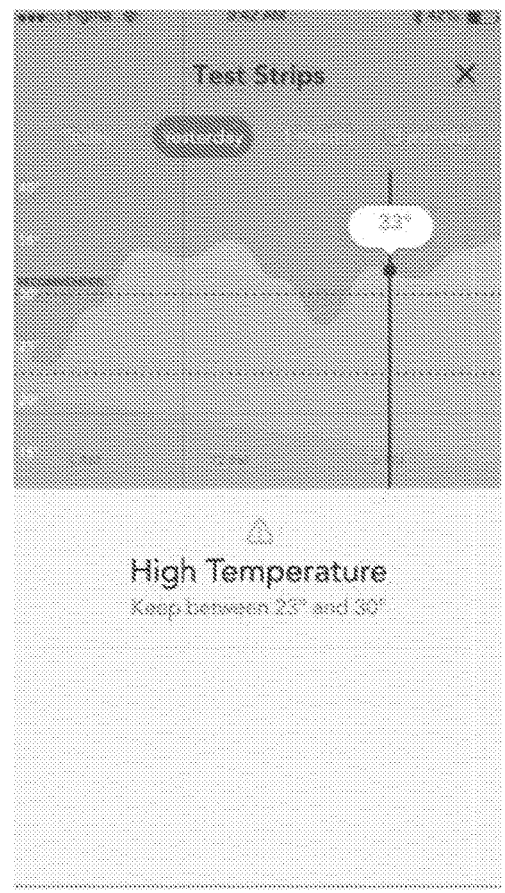
FIGURE 5S                    FIGURE 5T
500

500

500

METHODS AND SYSTEMS FOR MANAGING THE TEMPERATURE OF MEDICINES

CROSS-REFERENCE TO RELATED APPLICATIONS

This application claim priority to U.S. patent application Ser. No. 15/939,267 filed on Mar. 28, 2018. U.S. patent application Ser. No. 15/939,267 claims priority to U.S. provisional patent application No. 62/477,598 filed on 28 Mar. 2017. These patent applications are hereby incorporated by reference in its entirety.

BACKGROUND

Field of Invention

This invention relates generally to managing the temperature of medicines.

Background

Many diseases involve patient management of medicine consumption and self-testing of various patient states. For example, with diabetes, patients often test their blood glucose levels with test strips and glucose meters. Based on these results, patients may then take specified amounts of medicine such as insulin. Accordingly, medicine consumption and self-testing can be complex process with various points of error.

Additionally, medicines can degrade in certain conditions. For example, some temperatures need to be maintained in specified temperature ranges. Patients may not be able to constantly track medicine temperature. The same can be true for some testing instruments such as blood testing strips. Accordingly, improvements to the management of the temperatures of medication can improve patient self-management of health.

BRIEF SUMMARY OF THE INVENTION

A computer-implemented process useful for implementing a medometer management application including the step of, with a temperature sensor operative in the medometer, obtaining a temperature value of a medicine, a test strip and a medical device. With the medometer, the process includes the step of formatting the temperature value of the medicine for communication via a wireless network and communicate the formatted temperature value to a mobile device via a wireless network. With a medometer management application operative in the mobile device, the process includes the step of displaying the temperature value to a user.

Figure 1:
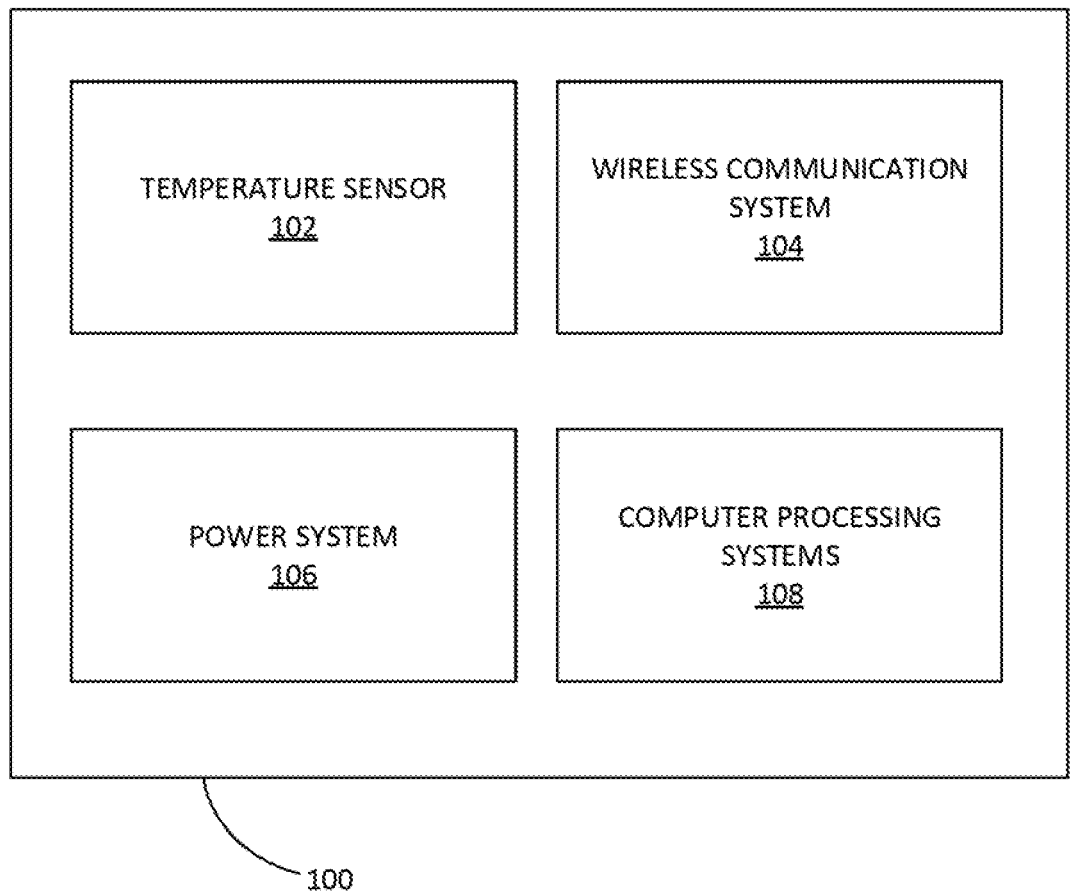
FIG. 1 illustrates an example schematic of a medometer device, according to some embodiments.

The Figures described above are a representative set and are not an exhaustive with respect to embodying the invention.

DESCRIPTION

Disclosed are a system, method, and article of manufacture for methods and systems of managing the temperature of medicines. The following description is presented to enable a person of ordinary skill in the art to make and use the various embodiments. Descriptions of specific devices, techniques, and applications are provided only as examples. Various modifications to the examples described herein can be readily apparent to those of ordinary skill in the art, and the general principles defined herein may be applied to other examples and applications without departing from the spirit and scope of the various embodiments.

Reference throughout this specification to 'one embodiment,' 'an embodiment,' 'one example,' or similar language means that a particular feature, structure, or characteristic described in connection with the embodiment is included in at least one embodiment of the present invention. Thus, appearances of the phrases 'in one embodiment,' 'in an embodiment,' and similar language throughout this specification may, but do not necessarily, all refer to the same embodiment.

Furthermore, the described features, structures, or characteristics of the invention may be combined in any suitable manner in one or more embodiments. In the following description, numerous specific details are provided, such as examples of programming, software modules, user selections, network transactions, database queries, database structures, hardware modules, hardware circuits, hardware chips, etc., to provide a thorough understanding of embodiments of the invention. One skilled in the relevant art can recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, and they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Definitions

Example definitions for some embodiments are now provided.

Application programming interface (API) can specify how software components of various systems interact with each other.

Bluetooth® is a wireless technology standard for exchanging data over short distances (using short-wavelength UHF radio waves in the ISM band from 2.4 to 2.485 GHz[3]) from fixed and mobile devices and building personal area networks (PANs).

Cloud computing can involve deploying groups of remote servers and/or software networks that allow centralized data storage and online access to computer services or resources. These groups of remote serves and/or software networks can be a collection of remote computing services.

Glucose meter is a medical device for determining the approximate concentration of glucose in the blood. It can also be a strip of glucose paper dipped into a substance and measured to the glucose chart. It can be used in home blood glucose monitoring (HBGM) by people with diabetes mellitus or hypoglycemia.

Inertial measurement unit (IMU) can be a device that measures acceleration and rotation.

Mobile device can include a handheld computing device that includes an operating system (OS), and can run various types of application software, known as apps. Example handheld devices can also be equipped with various context sensors (e.g. biosensors, physical environmental sensors, etc.), digital cameras, Wi-Fi, Bluetooth, and/or GPS capabilities. Mobile devices can allow connections to the Internet and/or other Bluetooth-capable devices, such as an automobile, a wearable computing system and/or a microphone headset. Exemplary mobile devices can include smart phones, tablet computers, optical head-mounted display (OHMD) (e.g. Google Glass®), virtual reality head-mounted display, smart watches, other wearable computing systems, etc.

Peltier effect is the presence of heating or cooling at an electrified junction of two different conductors. When a current is made to flow through a junction between two conductors, A and B, heat may be generated or removed at the junction. Thermoelectric cooling uses the Peltier effect to create a heat flux between the junction of two different types of materials. A Peltier cooler, heater, or thermoelectric heat pump is a solid-state active heat pump which transfers heat from one side of the device to the other, with consumption of electrical energy depending on the direction of the current.

Temperature sensors can include mechanical temperature sensors, electrical temperature sensors, integrated circuit sensors, medometers, etc.

Example Medometer Device

FIG. 1 illustrates an example schematic of a medometer device 100, according to some embodiments. Medometer device 100 can be stored with temperature-sensitive items. For example, medometer device 100 can be stored with medicines, test strips, medical devices (e.g. a glucometer, etc.). Medometer device 100 can include sensors to obtain information about these items. For example, medometer device 100 can include a temperature sensor 102. Temperature sensor 102 can measure thermal values, heat values, temperature values, etc. Temperature sensor 102 can communicate these measurements at periodic intervals to computer processing system 108. Computer processing system 108 can utilized wireless communication system 104 (e.g. a Bluetooth® system, etc.) to communicate to a medometer management application in a user local mobile device and/or other computing system with a wireless capability over local-wireless network 412. Alternatively, medometer device 100 can be coupled with a computing system via Universal Serial Bus (USB) or another wired-communication system. Power system 106 can include batteries and/or other applicable power sources. It is noted that other sensors (e.g. barometer sensors, light sensors, moisture sensors, location system, etc.) can be included in medometer 100 can operate in a manner similar to that of temperature sensor 102. Additionally, in some examples, a plurality of temperature sensors can be utilized as well. medometer device 100 can include light displays/indicators, speakers, haptic systems, etc.

Figure 2:
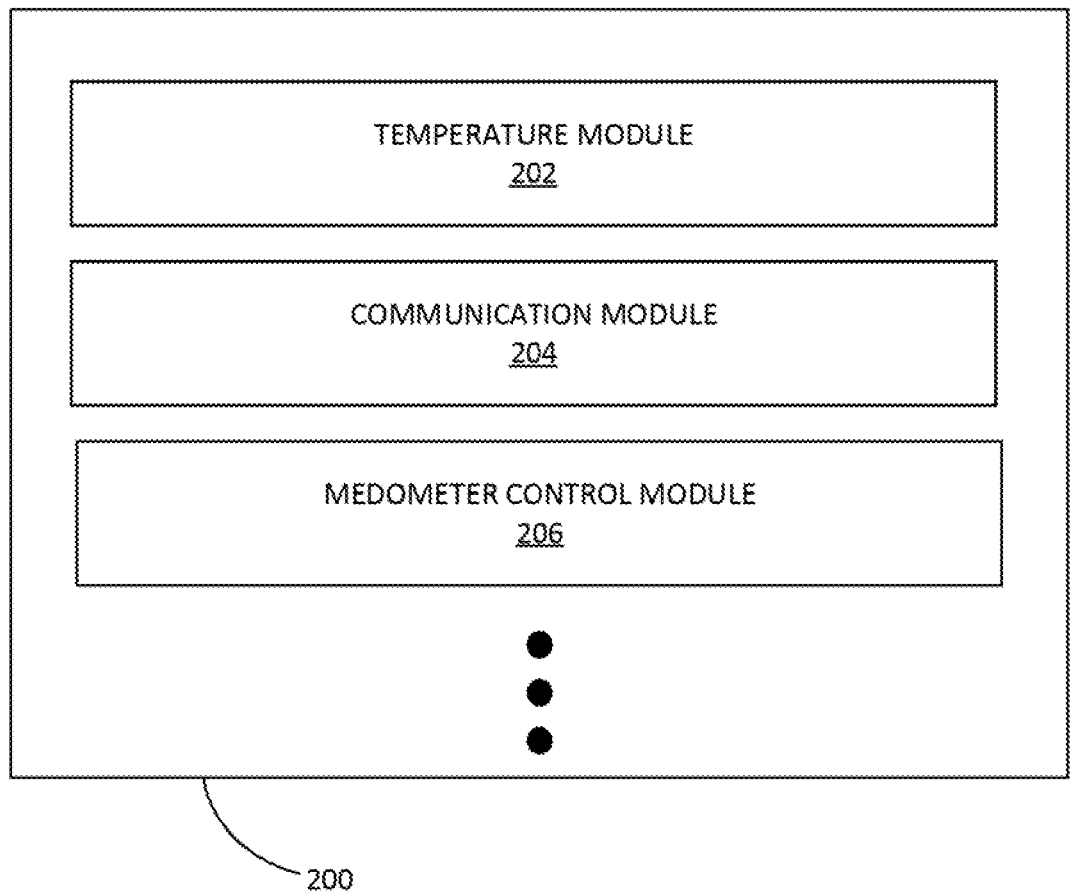
FIG. 2 illustrates an example logical view of a medometer device, according to some embodiments.

FIG. 2 illustrates an example logical view 200 of a medometer device 100, according to some embodiments. Temperature module 202 can include logic implemented in computer processing system 108 to control the operation of temperature sensor 102, as well as, obtain temperature data. Communication module 204 can format temperature data (as well as other metadata regarding the state of the medometer, battery data, etc.) for communication to a remote medometer management application. Medometer control module 206 can manage the operation of medometer device 100. For example, medometer control module 206 can place medometer device 100 in a sleep state during periods of inactivity, push notifications to a medometer management application when battery power is low, monitor and provide medometer device location to medometer management application, etc.

Figure 3:
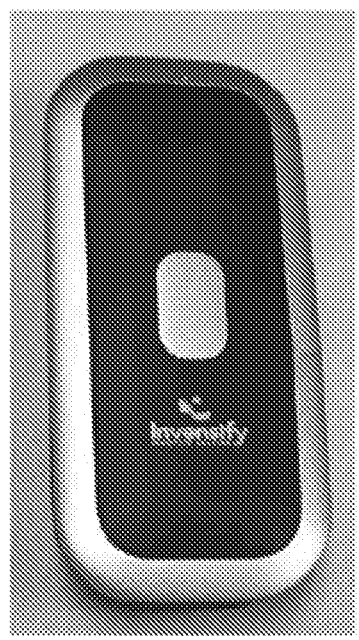
FIG. 3 illustrates an example image of another medometer device, according to some embodiments.

FIG. 3 illustrates example images of a (e.g. a smart-pouch temperature sensor) a medometer device 300, according to some embodiments. (It is noted that FIG. 6 of U.S. provisional patent application No. 62/477,598 filed on 28 Mar. 2017 and incorporated herein by reference, illustrates an example schematic diagram of a medometer device 100/300, according to some embodiments.) Medometer device 300 can include various temperature sensors. Medometer device 300 can be communicatively coupled (e.g. via a wireless network) with a user's mobile device. In one example, the wireless network can be a Bluetooth® wireless network. Accordingly, medometer device 300 can include various wireless networking systems, power sources (e.g. batteries, etc.). Medometer device 300 can periodically measure the temperature in a smart-pouch compartment that stores a medicine container. Medometer device 300 can periodically communicate the medicine container's smart-pouch compartment to a mobile device. Medometer device 300 can be water proof and/or water resistant. Medometer device 300 can periodically communicate a heart-beat signal to the local mobile device it is coupled with. In this way, should the medometer device 300 and local mobile device separate beyond a specified distance, the separation event can be noted by a medometer application in the mobile device. Medometer application can then note and record the location of the separation. This Information can be translated to geographical coordinates and presented to the user via an online mapping services (e.g. Google® maps, etc.).

Example Medometer Application

Figure 4:
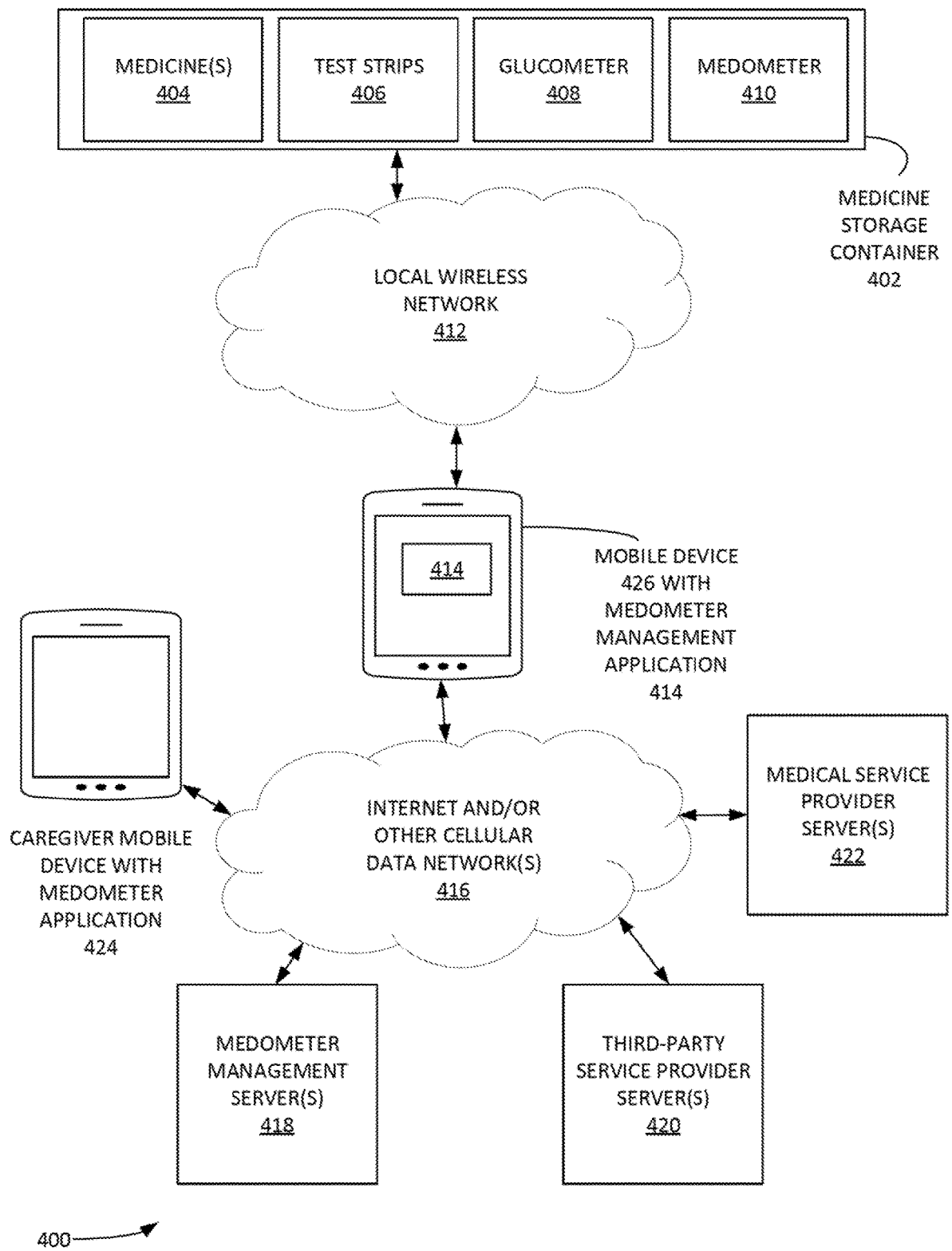
FIG. 4 illustrates an example system of a medometer management application, according to some embodiments.

FIG. 4 illustrates an example system 400 of a medometer management application 414, according to some embodiments. System 400 can include medicine storage container 402. Medicine storage container 402 can be used to store medications at a specified temperature. Medicine storage container 402 can be portable. For example, medicine storage container 402 can be carried by a user in a purse, book bag, suitcase, by hand, etc.

Medicine storage container 402 can include medicine(s) 404, test strips 406, glucometer 408, medometer 410, etc. Medometer 410 can continuously monitor the inner temperature of the medical-cooling case. Medometer 410 can communicate the temperature data over, in real time (e.g. assuming networking and processing latencies), to a medometer management application 414 in mobile device 426. Mobile device 426 can include an operating system (e.g. Android®, IOS®, etc.) via local WiFi network 408 (e.g. Bluetooth®, etc.). Medometer 404 can include a battery. The battery can have a battery life of thirty (30) days or more on a charge. The battery can also be recharged via a micro-USB system. Medometer 410 can include a red LED indicator that provides a warning that indicate when there is a need to re-charge.

Medometer management application 414 in mobile device 410 can enable the user to view the current temperature within the pouch in real time. Medometer management application 414 can enable the user to view a temperature graph of the pouch at the end of the day. Medometer management application 414 can perform analysis, providing a status on the viability of the medication based on the temperature fluctuations that it was exposed to throughout the day. Medometer management application 414 can enable the user to select the medications he/she is carrying in the pouch. Each medication, (such as insulin, Epinephrine, Bydureon, etc.) can have its own profile. This profile can include temperature ranges and the duration for which the medication can be used at that temperature. In the event that Medometer management application 414 detects that the temperature in medicine storage container 402 rises above or falls below the range of a specified medication and/or the medication reaches the length of time that it can remain in that temperature range, medometer management application 414 can implement an alert. For example, medometer management application 414 can cause an alert to appear on the mobile device 426. Alarms can be set for multiple medications. Medometer management application 414 can send an email to a secondary remote phone, alerting the user, parent, or caregiver that the temperature went outside the specified range. This allows a parent or caregiver to intervene and ensure the safety of the medication. Medometer management application 414 can locate and medometer temperature sensor(s) 406. In the event that the user can't find medicine storage container 402 (and/or a smart-medicine wallet, etc.), medometer management application 414 can show them a map location of medicine storage container 402. Medometer management application 414 can alert the user via mobile device 410 (in addition to the alert on the device) when the battery needs recharging as well. Example screen shots of medometer management application 414 are provided infra.

System 400 can include various computer and/or cellular data networks 416. Computer and/or cellular data networks 416 can include the Internet, cellular data networks, local area networks, enterprise networks, etc. Networks 416 can be used to communicate messages and/or other information from the various entities of system 400.

System 400 can include various servers for augmenting the functionality of medometer application. Medometer management server(s) 414 can, for example, implement the functionalities of medometer application. Medometer management server(s) 414 can include tables of medicines and their respective temperature management data. Medometer management server(s) 414 can obtain additional information form third-party servers 420. For example, third-party server 420 can be geo-mapping services that provides maps enabling a user to navigate to a lost medicine storage container 402. Medometer management server(s) 414 can include additional functionalities such as, Inter allo, web servers, calculators, time-clocks, medication data, statistical calculation systems, database management systems, etc. Medometer management server(s) 414 can communicate a user's medical temperature data to the user's medical service providers (e.g. medical-service provider's server(s) 422) and/or caregiver mobile device 424 with a care-giver version of the medometer management application 414. Based on the incoming data from medometer management application 414, medometer management server(s) 414 can push alerts, historical data, etc. to medical-service provider's server(s) 422 and/or caregiver mobile device 424 (e.g. as shown in FIGS. 5 A-X).

FIGS. 5 A-X illustrates an example set of screenshots 500 for implementing a medometer management application, according to some embodiments. As shown, medometer management application can include various functionalities for monitoring medication state (e.g. temperature, expiry date, etc.), as well as, biological testing tool (e.g. test strips, etc.) state. Medometer management application can include disease management tools and functionalities as well. Medometer management application can include additional functionalities. For example, users can include personal notes, comment on data, input diet data, input mental state data, treatment side-effect data, etc. Medometer management application can include a medicine intake scheduling system and timer that alerts the user when to take specified medicines and/or perform specified tests. Medometer management application can communicatively couple with a glucometer and/or other medical devices (e.g. USB cable, Wi-Fi, cellular networks, etc.). Medometer management application can include a library of medicines (e.g. diabetes treatment medicines, etc.). The library of medicines can be automatically updated by a remote server. Medometer management application can be set to automatically alert medical caregivers when a specified parameter is detected (e.g. low or high glucose levels, a specified side effect, etc.). Side-effect triggers can be automatically obtained from the digital library of medicines when the user inputs into the medometer management application that the use is taking said medicine.

Figure 5A:
FIGS. 5 A-X illustrates an example set of screenshots for implementing a medicine temperature management application, according to some embodiments.
Figure 5B:
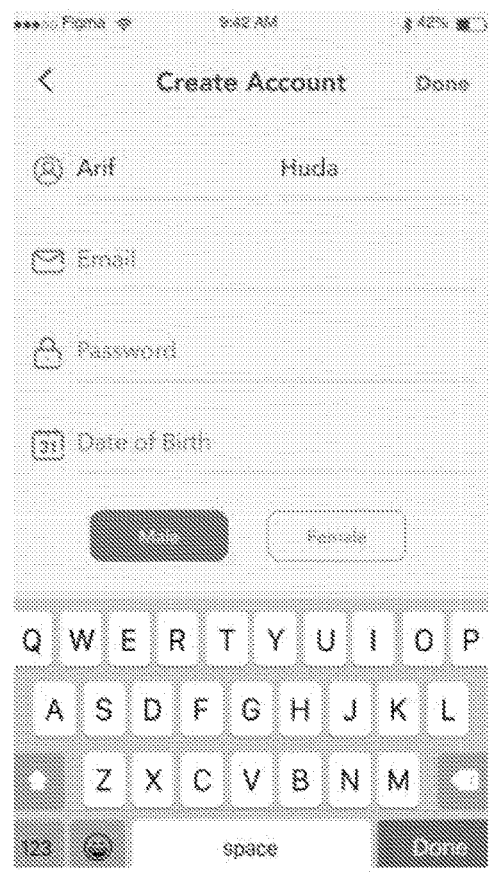

FIG. 5A illustrates an example initial page for the medometer management application. FIG. 5B illustrates an example account creation page.

A user can couple the medometer management application with a variety of devices such as one or more medometers, smart-refrigerators, temperature sensors, etc. FIG. 5C illustrates an example screenshot indicating that a coupling operation is in progress.

Figure 5E:
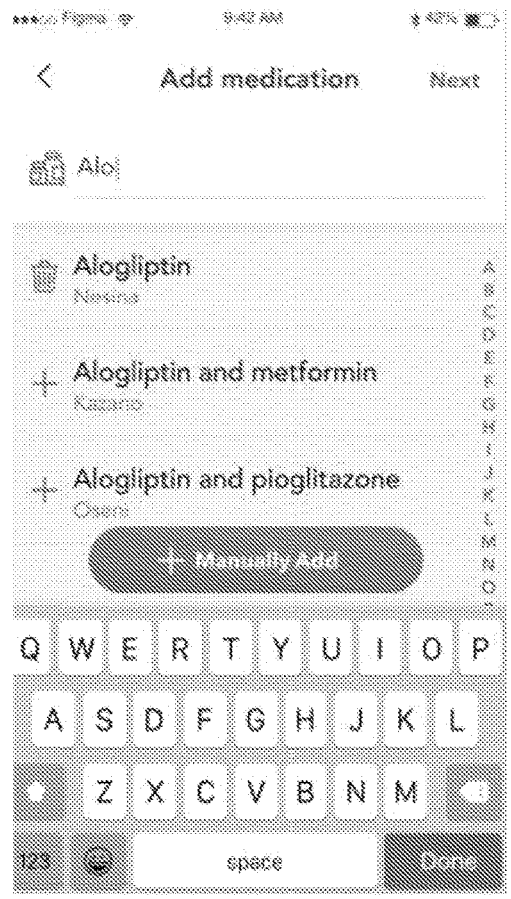
Figure 5F:
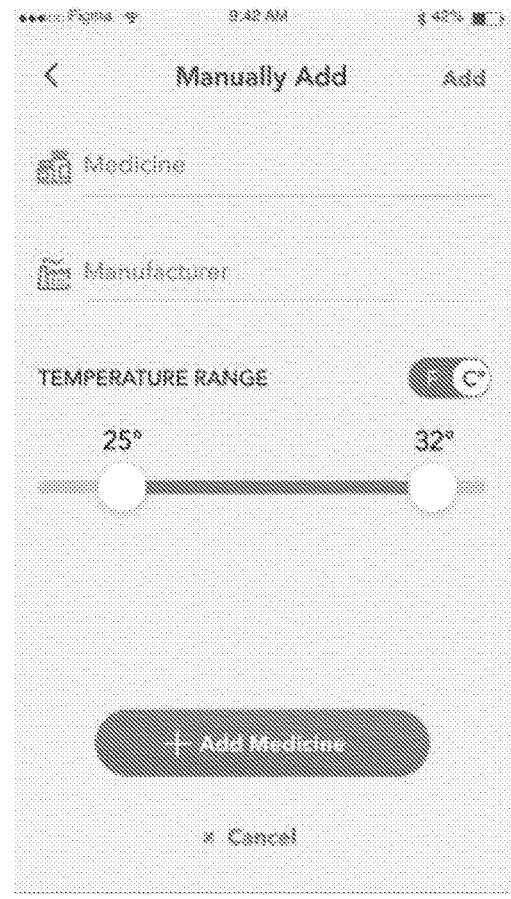
Figures 5G, 5H:
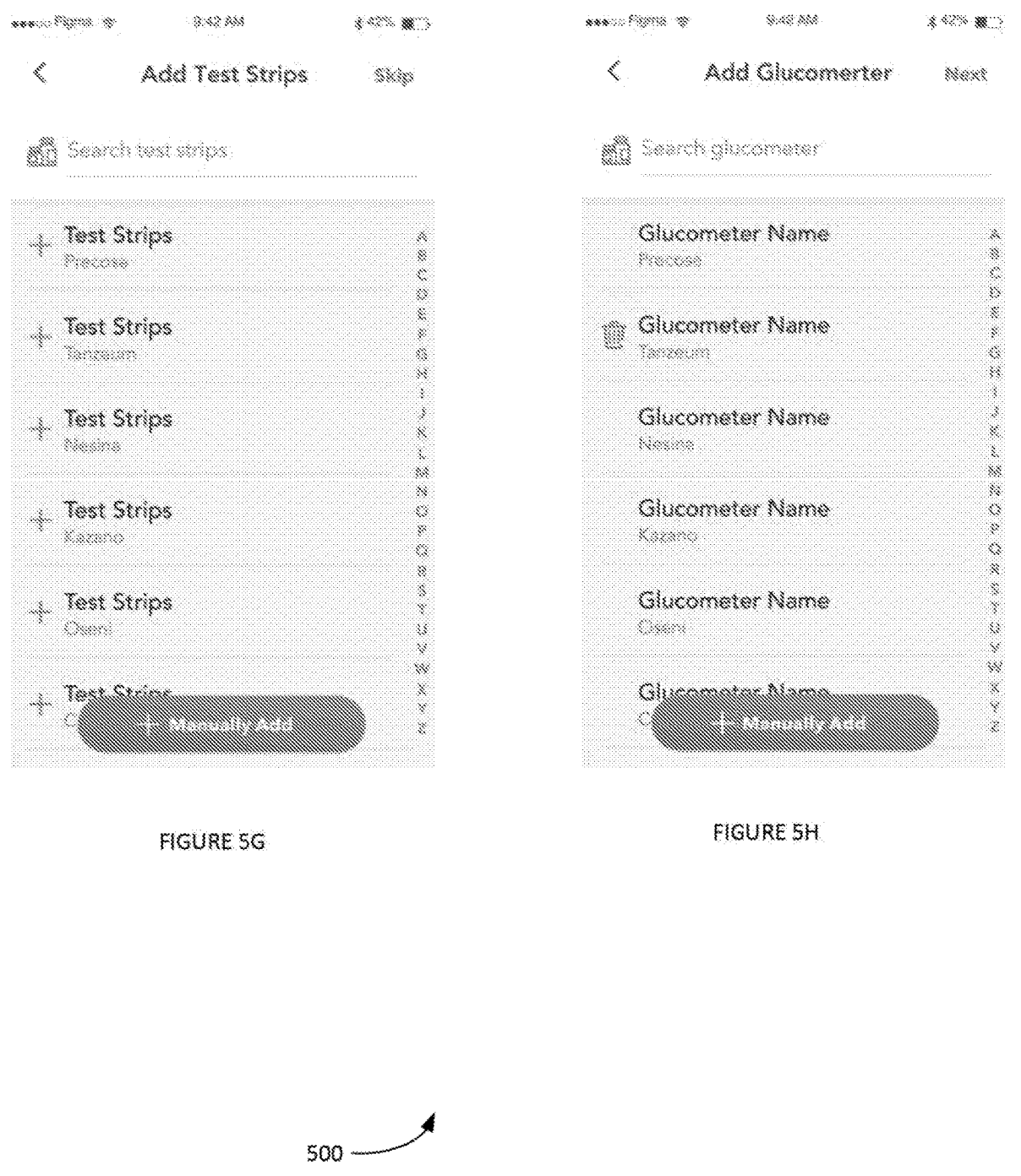
Figure 5M:
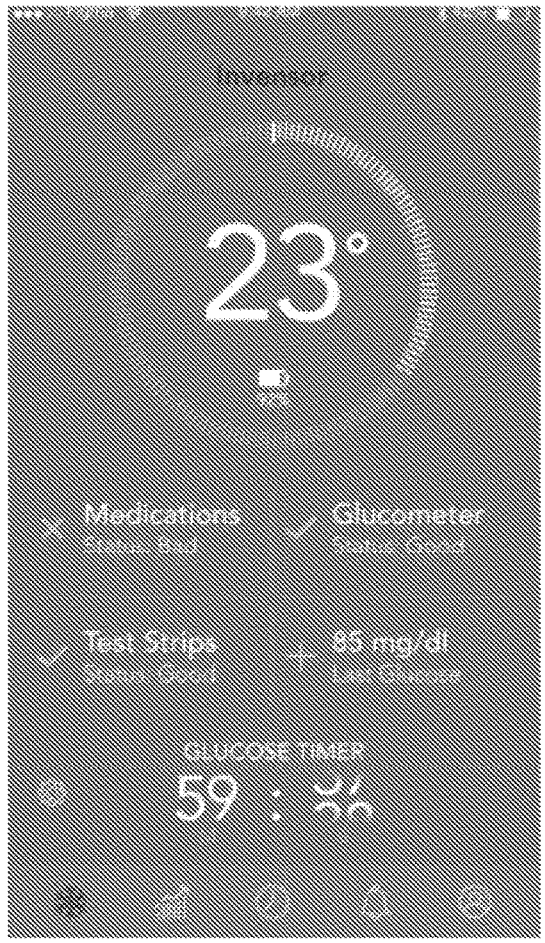
Figure 5N:

As shown in FIG. 5D, a user can select medications to be monitored. The medometer management application can provide a list of medications. The list can include the generic and/or proprietary names of the various medications. The medometer management application can include a table of the proper storage states (e.g. temperature, pressure, light sensitivity, expiration periods, etc.) of the medications and/or related biological testing tools. The medometer can include sensors to monitor the proper storage states. The medications and/or related biological testing tools can be searched for via alpha-numeric input as shown in FIG. 5E. Additionally, users can remove medications and/or related biological testing tools from the list. Users can also manually input proper storage state attributes as shown in FIG. 5F.

FIG. 5G shows a specific example of a list of test strips that can be searched for and selected. Once selected, the medometer and medometer management application can monitor the state of said test strips. FIG. 5H shows a specific example of a list of glucometers that can be searched for and selected. Once selected, the state of the glucometer can be monitored. Glucometer data can be electronically communicated to the medometer management application. Additionally, it is noted that other types of medical device data can also be obtained and monitored by the medometer management application. Accordingly, the glucometer embodiments are provided by way of example and not of limitation. FIG. 5I illustrates an example of using the medometer management application to set the application data ranges for a glucometer coupled with the medometer management application.

Users can share medometer management application data with selected caregivers. FIGS. 5 J-K illustrate an example of a medometer management application interface that enables users to select and/or manually input caregiver information. Medometer management application can then be uploaded to a caregiver's mobile device to review the user's medometer management application data.

FIGS. 5 L-N illustrate example home screens for a medometer management application. The home screen can include various clickable user-interface elements. For example, a user can click on a medication section to display a current medication list for the user. Medication status (e.g. current temperature, historical temperature, etc.) can also be accessed. A user can click on a test strip section to display a current test strip list for the user. Test strip status (e.g. current temperature, historical temperature, etc.) can also be accessed. A user can click on a glucose meter section to display a current glucose meter data for the user. Historical glucose meter data can also be accessed. The home screen can display the current status (e.g. 'good', 'warning', 'bad', etc.) of the medications, test strips, glucose meter, etc. that is currently being monitored by the medometer management application. The status can be a function of the current state of the medications, test strips, glucose meter, etc. The background color of the home screen can be updated to indicated said status (e.g. green with 'good' status, yellow with 'warning' status, red with 'bad' status, etc.). A glucose timer can also be included in the homepage.

Figure 5O:
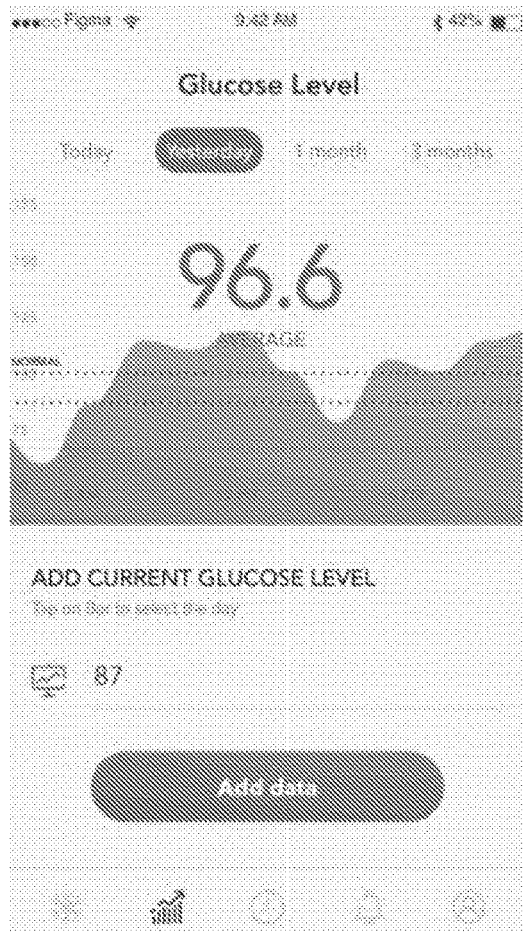
Figure 5P:
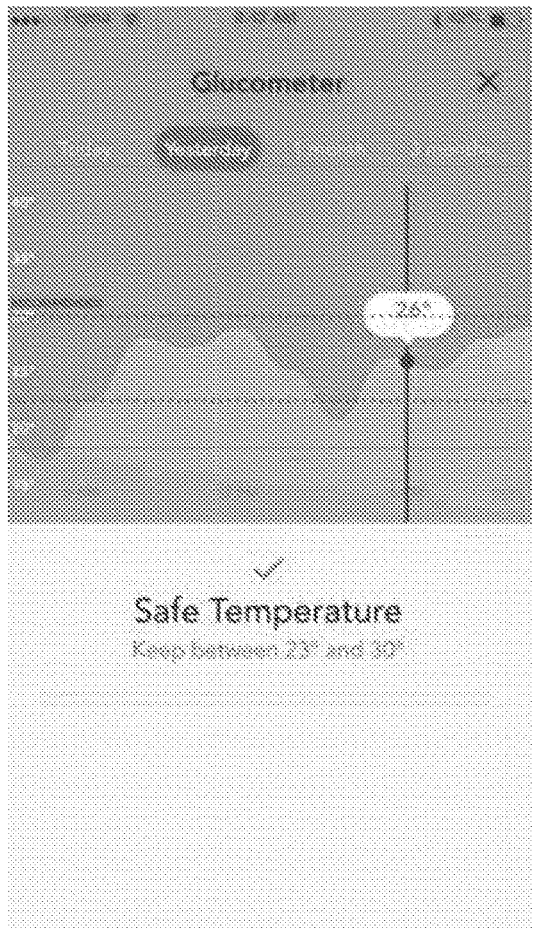
Figure 5Q:
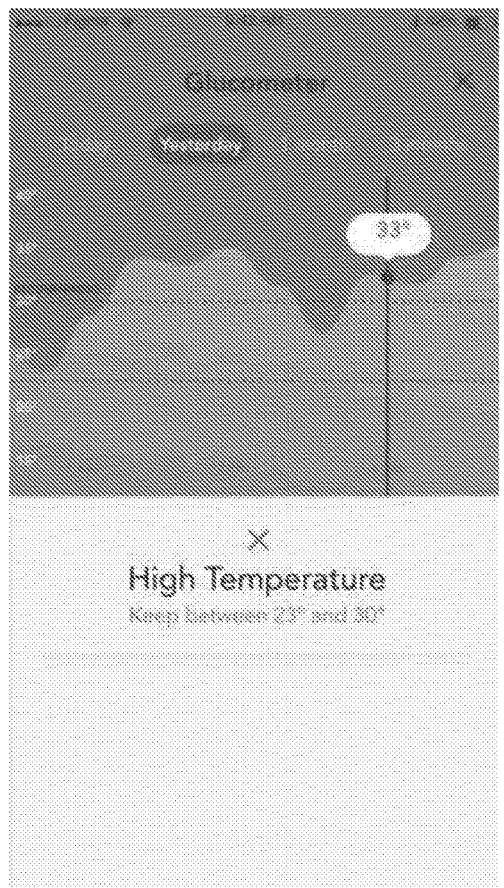
Figure 5R:
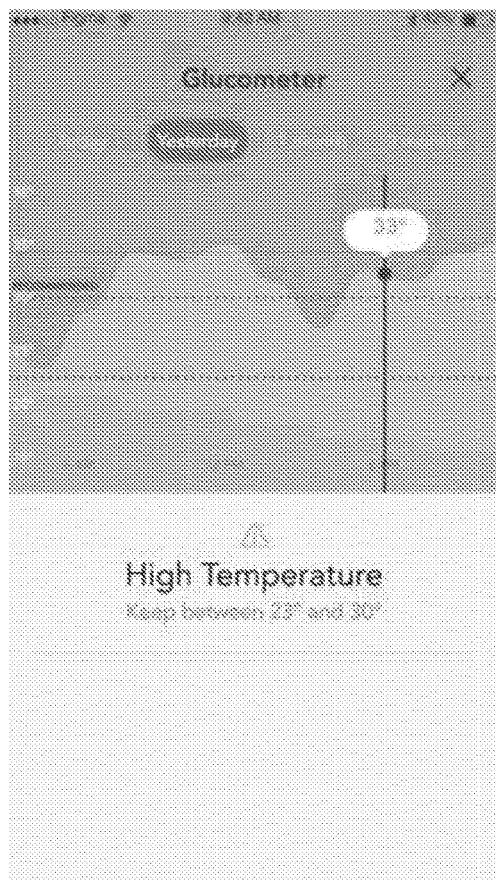
Figure 5U:
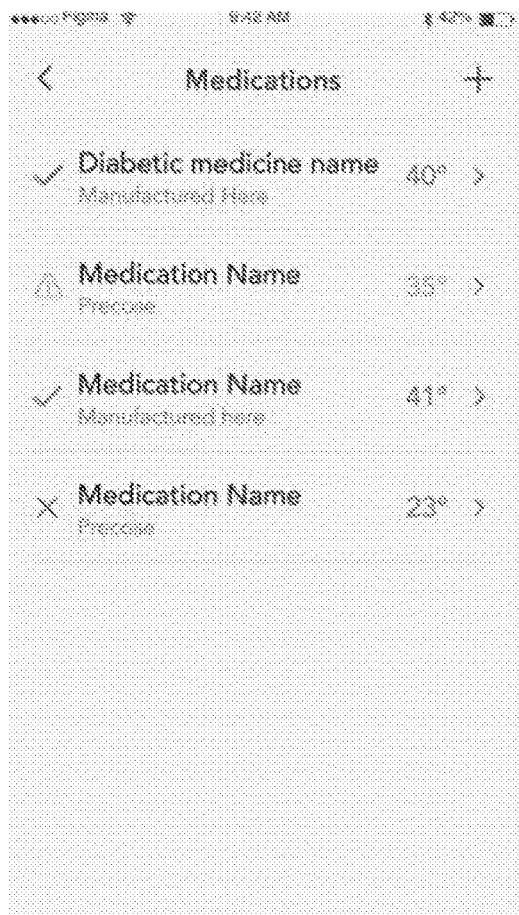
Figure 5V:
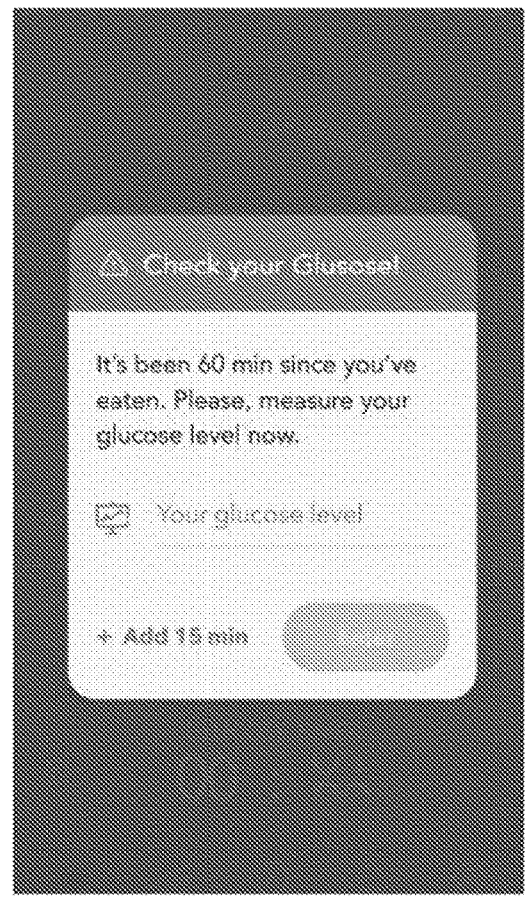
Figure 5W:
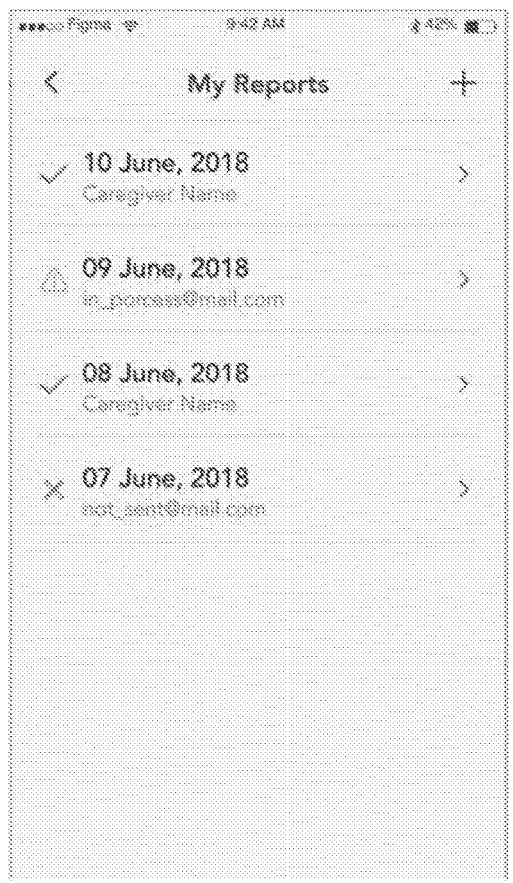
Figure 5X:
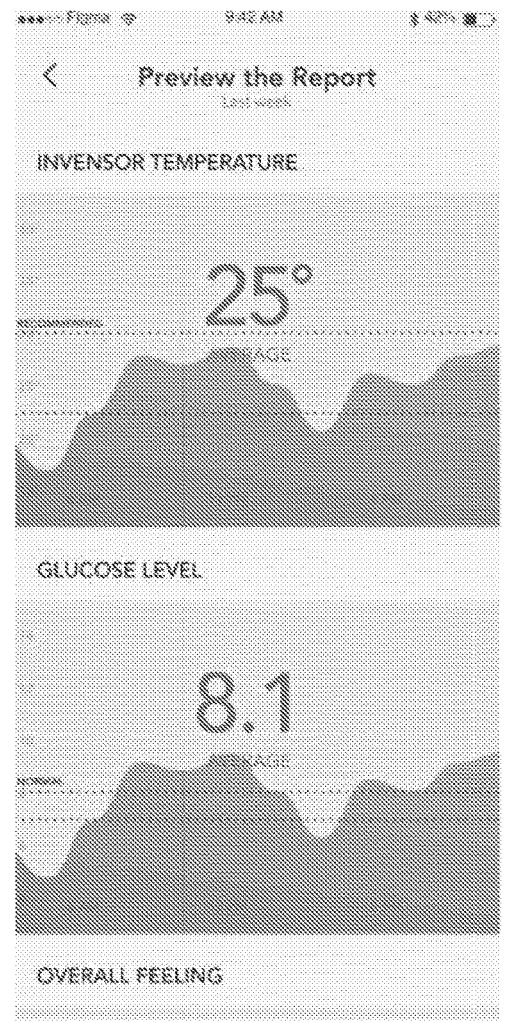

Medication data, test strip data, glucose meter data can be analyzed, and statistical data derived as well. These statistical and/or historical values can be displayed medometer management application. For example, FIG. 5O illustrates an example glucose level data display. As shown, a user can review and compare the glucose level dynamics with a variety of time ranges. Users can also manually add glucose level data directly into medometer management application.

FIGS. 5 P-R illustrate an example graphical display of the glucometer temperature data. The display can indicate that the glucometer temperature has been within or outside the allowable temperature parameters. Again, the historical and/or current state of the glucometer can be indicated with a background color. FIGS. 5 S-T illustrate an example graphical display of the test strip temperature data in a similar manner. FIGS. 5 U-V illustrate an example graphical display of the medicine temperature data in a similar manner as well. As shown in FIG. 5V, various medicine, test stripe and/or glucose/meter parameters can trigger push notification(s) from medometer management application. Push notifications can be communicated (e.g. via text message, push message, email, etc.) to caregivers, physicians, relatives, school employees, law enforcement, etc. push notifications can cause the medometer management application to alert the user (e.g. pop up window, sound alert, haptic alert, etc.) when a specific action should be taken. This data can also be communicated to a data store for later retrieval and analysis. This data can be used to generate reports as well. For example, FIG. 5W illustrates an interface that can be used to generate and send said reports. Report data can also be symbolized for graphical display as shown in FIG. 5V.

Example Computer Architecture and Systems

Figure 6:
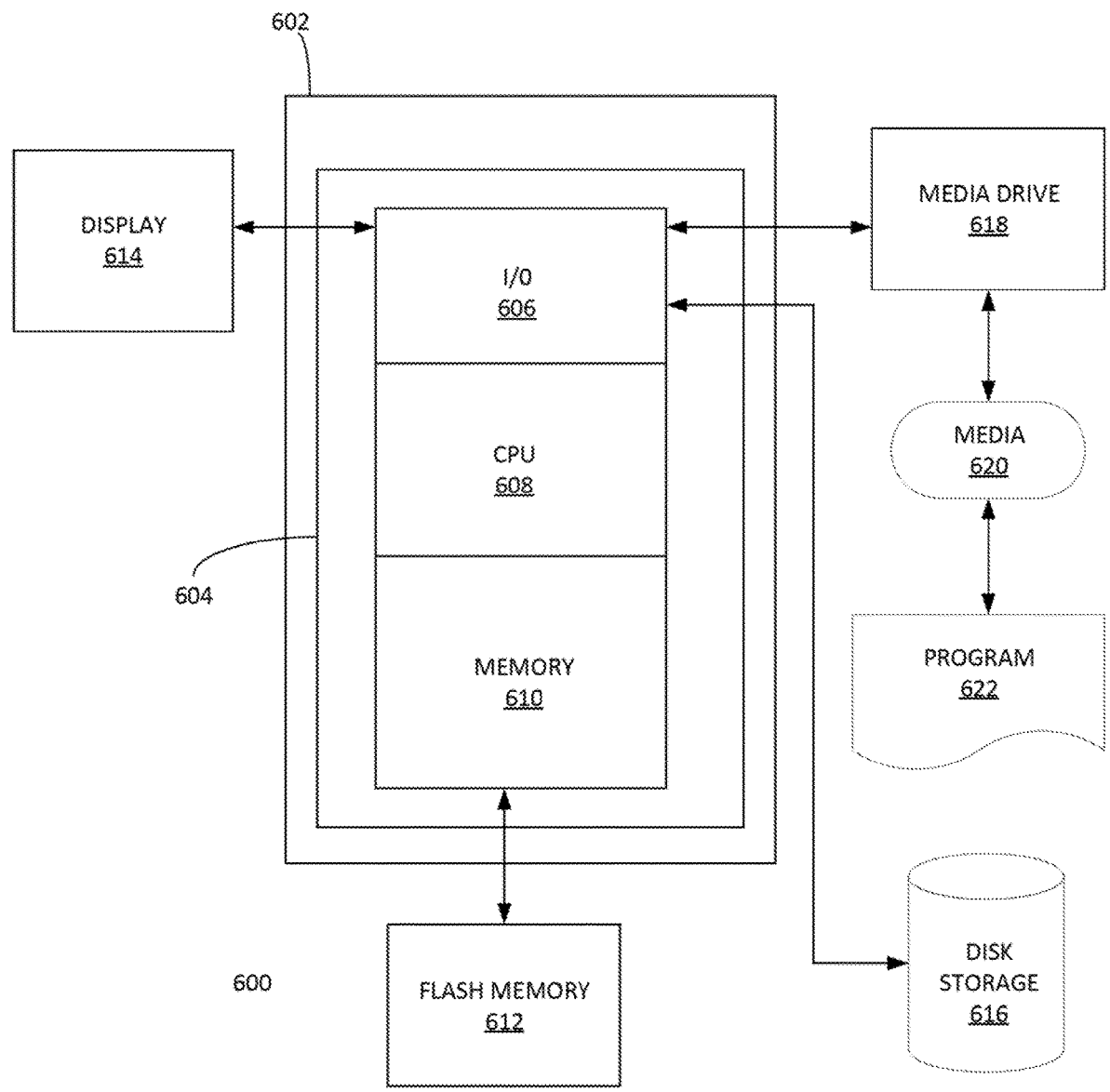
FIG. 6 depicts an exemplary computing system that can be configured to perform any one of the processes provided herein.

FIG. 6 depicts an exemplary computing system 600 that can be configured to perform any one of the processes provided herein. In this context, computing system 600 may include, for example, a processor, memory, storage, and I/O devices (e.g., monitor, keyboard, disk drive, Internet connection, etc.). However, computing system 600 may include circuitry or other specialized hardware for carrying out some or all aspects of the processes. In some operational settings, computing system 600 may be configured as a system that includes one or more units, each of which is configured to carry out some aspects of the processes either in software, hardware, or some combination thereof.

FIG. 6 depicts computing system 600 with a number of components that may be used to perform any of the processes described herein. The main system 602 includes a motherboard 604 having an I/O section 606, one or more central processing units (CPU) 608, and a memory section 610, which may have a flash memory card 612 related to it. The I/O section 606 can be connected to a display 614, a keyboard and/or other user input (not shown), a disk storage unit 616, and a media drive unit 618. The media drive unit 618 can read/write a computer-readable medium 620, which can contain programs 622 and/or data. Computing system 600 can include a web browser. Moreover, it is noted that computing system 600 can be configured to include additional systems in order to fulfill various functionalities. Computing system 600 can communicate with other computing devices based on various computer communication protocols such a Wi-Fi, Bluetooth® (and/or other standards for exchanging data over short distances includes those using short-wavelength radio transmissions), USB, Ethernet, cellular, an ultrasonic local area communication protocol, etc.

Figure 7:
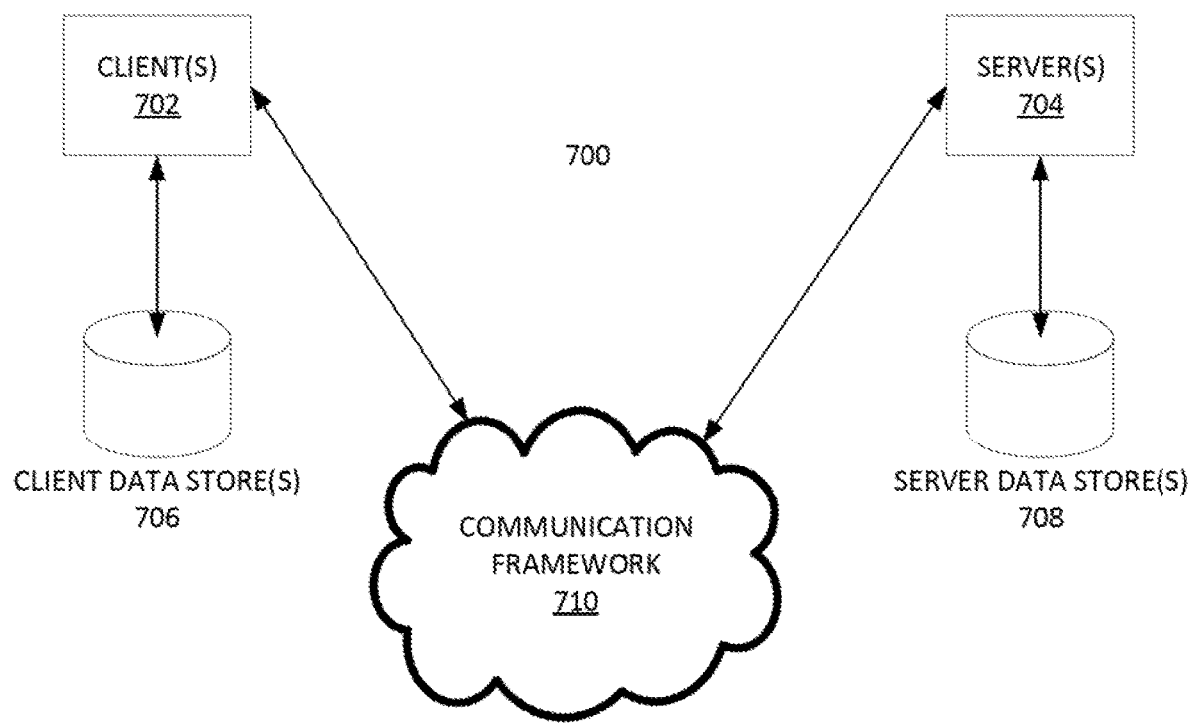
FIG. 7 is a block diagram of a sample computing environment that can be utilized to implement various embodiments.

FIG. 7 is a block diagram of a sample computing environment 700 that can be utilized to implement various embodiments. The system 700 further illustrates a system that includes one or more client(s) 702. The client(s) 702 can be hardware and/or software (e.g., threads, processes, computing devices). The system 700 also includes one or more server(s) 704. The server(s) 704 can also be hardware and/or software (e.g., threads, processes, computing devices). One possible communication between a client 702 and a server 704 may be in the form of a data packet adapted to be transmitted between two or more computer processes. The system 700 includes a communication framework 710 that can be employed to facilitate communications between the client(s) 702 and the server(s) 704. The client(s) 702 are connected to one or more client data store(s) 706 that can be employed to store information local to the client(s) 702. Similarly, the server(s) 704 are connected to one or more server data store(s) 708 that can be employed to store information local to the server(s) 704. In some embodiments, system 700 can instead be a collection of remote computing services constituting a cloud-computing platform.

Figure 8:
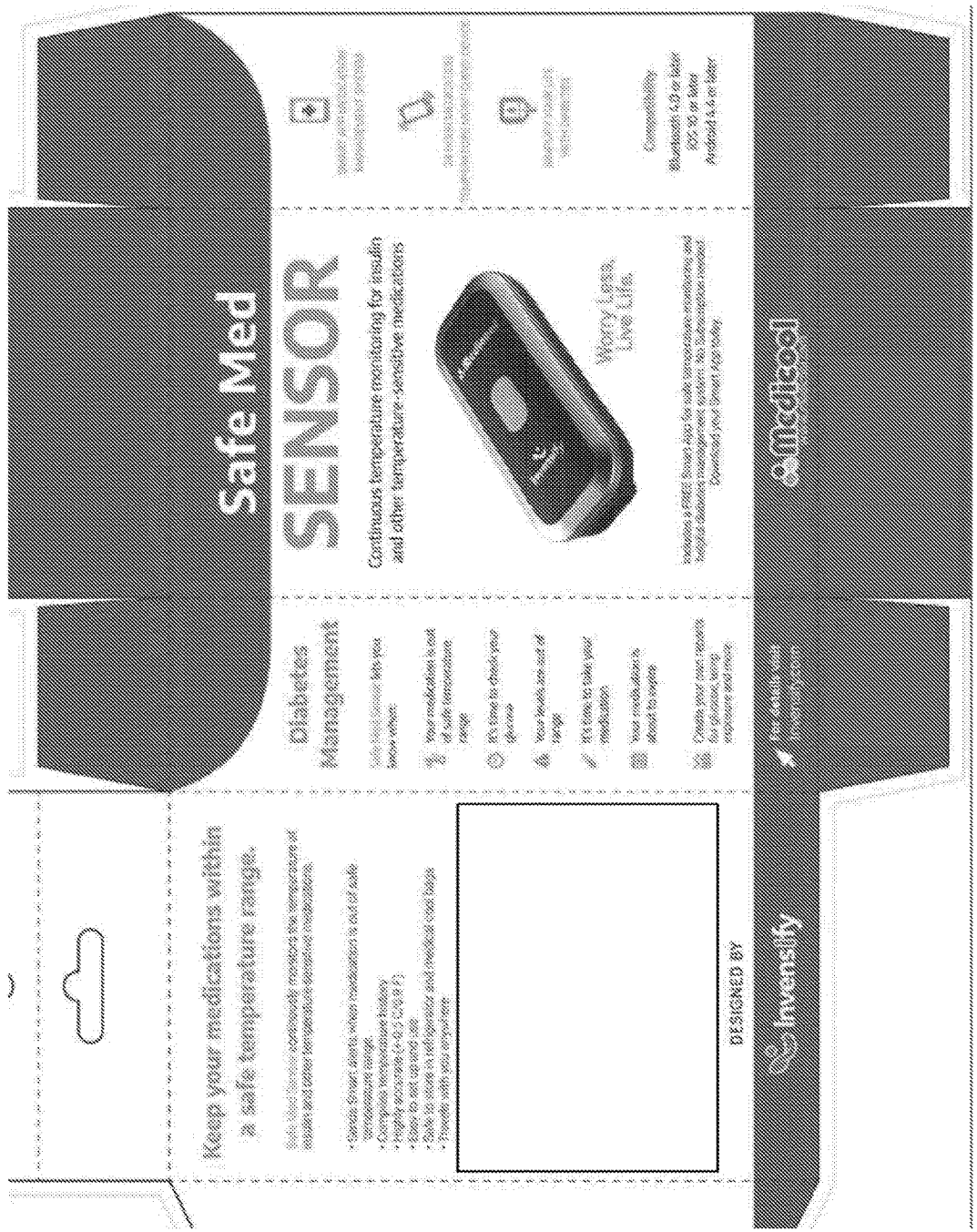
FIG. 8 illustrates an example medicine storage container, according to some embodiments.

FIG. 8 illustrates an example medicine storage container 800, according to some embodiments. Medicine storage container 800 can store a medometer and/or other temperature sensitive materials/devices such as, inter alia: glucometer(s), test strip(s), temperature-sensitive medicines, etc.

CONCLUSION

Although the present embodiments have been described with reference to specific example embodiments, various modifications and changes can be made to these embodiments without departing from the broader spirit and scope of the various embodiments. For example, the various devices, modules, etc. described herein can be enabled and operated using hardware circuitry, firmware, software or any combination of hardware, firmware, and software (e.g., embodied in a machine-readable medium).

In addition, it can be appreciated that the various operations, processes, and methods disclosed herein can be embodied in a machine-readable medium and/or a machine accessible medium compatible with a data processing system (e.g., a computer system), and can be performed in any order (e.g., including using means for achieving the various operations). Accordingly, the specification and drawings are to be regarded in an illustrative rather than a restrictive sense. In some embodiments, the machine-readable medium can be a non-transitory form of machine-readable medium.

What is claimed as new and desired to be protected by Letters Patent of the United States is:

1. A computer-implemented process useful for implementing a medometer management application comprising:
    with a temperature sensor operative in the medometer:
        obtaining a temperature value of a medicine, a test strip and a medical device;
    with the medometer
        formatting the temperature value of the medicine for communication via a wireless network, and
        communicating the formatted temperature value to a mobile device via a wireless network, and
    with a medometer management application operative in the mobile device:
        displaying the temperature value to a user.

2. The computer-implemented method of claim 1, wherein the medometer management application:
    determines that the temperature value is out of at least one specified temperature range for the medicine, the test strip or the medical device.

3. The computer-implemented method of claim 2, wherein the medometer management application:
    with the mobile device, display a warning indicator that the temperature value has exceeded the at least one specified temperature range for the medicine, the test strip or the medical device.

4. The computer-implemented method of claim 3, wherein the medical device comprises a glucometer.

5. The computer-implemented method of claim 3, wherein the medometer management application comprises a list of diabetes treatment medications that are displayed to the user.

6. The computer-implemented method of claim 5, wherein the list of diabetes treatment medications comprises a set of specified temperature ranges for each medicine.

7. The computer-implemented method of claim 6, wherein the medical device comprises a glucometer.

8. The computer-implemented method of claim 7, further comprising:
    receiving a dietary input from the user, a glucometer reading of the user's blood glucose reading from the glucometer or a user state description from the user with the medometer management application.

9. The computer-implemented method of claim 8, further comprising:
    communicating the dietary input from the user, the glucometer reading of the user's blood glucose reading from the glucometer or the user state description from the user with the medometer management application and the temperature sensor values to a mobile device of a specified caregiver.

10. A computerized system useful for implementing a medometer management application comprising:
    at least one processor configured to execute instructions;
    at least one memory containing instructions that when executed on the at least one processor, causes the at least one processor to perform operations that:
        with a temperature sensor operative in the medometer:
            obtain a temperature value of a medicine, a test strip and a medical device;
        with the medometer:
            format the temperature value of the medicine for communication via a wireless network, and
            communicate the formatted temperature value to a mobile device via a wireless network, and
        with a medometer management application operative in the mobile device:
            display the temperature value to a user.

11. The computerized system of claim 10, wherein the medometer management application:
    determines that the temperature value is out of at least one specified temperature range for the medicine, the test strip or the medical device.

12. The computerized system of claim 10, wherein the medometer management application:
    with the mobile device, displays a warning indicator that the temperature value has exceeded the at least one specified temperature range for the medicine, the test strip or the medical device.

13. The computerized system of claim 12, wherein the medical device comprises a glucometer.

14. The computerized system of claim 13, wherein the medometer management application comprises a list of diabetes treatment medications that are displayed to the user.

15. The computerized system of claim 14, wherein the list of diabetes treatment medications comprises a set of specified temperature ranges for each medicine.

* * * * *